US011389118B2

(12) United States Patent
Ghose et al.

(10) Patent No.: US 11,389,118 B2
(45) Date of Patent: Jul. 19, 2022

(54) SYSTEM AND METHOD FOR BREATHING PATTERN EXTRACTION FROM PPG SIGNALS

(71) Applicant: Tata Consultancy Services Limited, Mumbai (IN)

(72) Inventors: Avik Ghose, Kolkata (IN); Shalini Mukhopadhyay, Kolkata (IN); Dibyanshu Jaiswal, Kolkata (IN); Dhaval Satish Jani, Rockville, MD (US)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 308 days.

(21) Appl. No.: 16/179,807

(22) Filed: Nov. 2, 2018

(65) Prior Publication Data

US 2019/0133537 A1 May 9, 2019

(30) Foreign Application Priority Data

Nov. 3, 2017 (IN) .............................. 201721039317

(51) Int. Cl.
*A61B 5/00* (2006.01)
*A61B 5/024* (2006.01)
*A61B 5/08* (2006.01)

(52) U.S. Cl.
CPC ........ *A61B 5/7278* (2013.01); *A61B 5/02416* (2013.01); *A61B 5/02438* (2013.01);
(Continued)

(58) Field of Classification Search
CPC ....... A61B 5/08; A61B 5/0803; A61B 5/0816; A61B 5/0205; A61B 5/02416;
(Continued)

(56) References Cited

U.S. PATENT DOCUMENTS 8,622,922 B2    1/2014  Banet et al.
9,179,876 B2 *  11/2015 Ochs .................... A61B 5/0816
(Continued)

FOREIGN PATENT DOCUMENTS

WO    WO-03/005893 A2    1/2003

OTHER PUBLICATIONS

D. Li, H. Zhao, S. Dou, A new signal decomposition to estimate breathing rate and heart rate from photoplethysmography signal Biomed. Signal Process. Control, 19 (2015), pp. 89-95.*
G. Angius and L. Raffo, "Cardiovascular disease and sleep apnoea: A wearable device for PPG acquisition and research aims," 2012 Computing in Cardiology, Krakow, Poland, 2012, pp. 513-516. (Year: 2012).*
(Continued)

*Primary Examiner* — Sean P Dougherty
*Assistant Examiner* — Kyle W. Kretzer
(74) *Attorney, Agent, or Firm* — Finnegan, Henderson, Farabow, Garrett & Dunner LLP (57) ABSTRACT

A system and method for extracting breathing patterns from PPG signals are provided. The method includes designing a filter for extracting breathing patterns from PPG signals. Designing the filter includes defining filter specifications for extraction of breathing pattern from the PPG signals. Herein, the filter specifications includes a type, an order and a cut-off frequency of the filter. Designing the filter further includes generating a transfer function associated with the filter specifications, and computing a plurality of filter coefficients using filtfilt function for allowing filtering of the PPG signals. Using the filter comprising the plurality of filter coefficients, a filtered PPG signal is generated by removing DC component from PPG signals obtained from a wearable device being worn by a subject. The filtered PPG signal is indicative of the breathing pattern of the subject.

6 Claims, 6 Drawing Sheets

(52) U.S. Cl.
CPC ............ *A61B 5/0816* (2013.01); *A61B 5/681* (2013.01); *A61B 5/721* (2013.01); *A61B 5/7203* (2013.01); *A61B 5/725* (2013.01); *A61B 5/7221* (2013.01); *A61B 5/7257* (2013.01); *A61B 5/742* (2013.01); *A61B 5/7207* (2013.01); *A61B 2562/0219* (2013.01)

(58) Field of Classification Search
CPC ....... A61B 5/681; A61B 5/6824; A61B 5/721; A61B 5/725; A61B 5/7257; A61B 5/7225
See application file for complete search history.

(56) References Cited

U.S. PATENT DOCUMENTS

| | | | | |
|---|---|---|---|---|
| 9,943,267 | B2* | 4/2018 | Ferber | A61B 5/024 |
| 10,004,427 | B1* | 6/2018 | Shoeb | A61B 5/0816 |
| 2012/0127157 | A1* | 5/2012 | Adler | A61B 5/0024 345/419 |
| 2017/0245808 | A1* | 8/2017 | Jain | A61B 5/746 |

OTHER PUBLICATIONS

M. Hickey, J. P. Phillips and P. A. Kyriacou, "The effect of vascular changes on the photoplethysmographic signal at different hand elevations," Physiological Measurement, vol. 36, No. 3, 2015, pp. 425-440 (Year: 2015).*

Fleming, Susannah G., and Lionel Tarassenko. "A comparison of signal processing techniques for the extraction of breathing rate from the photoplethysmogram." Int. J. Biol. Med. Sci 2.4 (2007): 232-236. (Year: 2007).*

Park et al. (2014). "Real-time estimation of respiratory rate from a photoplethysmogram using an adaptive lattice notch filter," BioMedical Engineering OnLine, vol. 13, No. 170; pp. 1-16. located at https://biomedical-engineering-online.biomedcentral.com/track/pdf/10.1186/1475-925X-13-170?site=biomedical-engineering-online.biomedcentral.com.

Angius et al. (2012). "Cardiovascular Disease and Sleep Apnoea: a Wearable Device for PPG Acquisition and Research Aims," *2012 Computing in Cardiology, IEEE*, vol. 39, pp. 513-516, located at http://cinc.org/archives/2012/pdf/0513.pdf.

* cited by examiner

(a) Normal Breathing Pattern

SYSTEM AND METHOD FOR BREATHING PATTERN EXTRACTION FROM PPG SIGNALS

PRIORITY CLAIM

This U.S. patent application claims priority under 35 U.S.C. § 119 to: India Application No. 201721039317, filed on Nov. 3, 2017. The entire contents of the aforementioned application are incorporated herein by reference.

TECHNICAL FIELD

The present disclosure in general relates to extraction of breathing patterns from photoplethysmogram (PPG) signals, and more particularly to system and method for designing a filter to extract breathing patterns from PPG signals.

BACKGROUND

Today's sedentary work environment and an unhealthy eating lifestyle has attracted a spectrum of cardiopulmonary diseases. As of 2017, cardiac diseases are responsible for maximum deaths in United States, with chronic respiratory disorders ranking no. 3. According to the CDC, more than 40% of such disorders lead to deaths outside the hospital, the reason being failure to detect early warning signs. It has thus become imperative to be able to not only detect the actual symptoms of such disorders beforehand, but also to detect the possibility of any abnormality in the cardiopulmonary system of the body.

Cardiopulmonary Exercise Test (CPET) is an important clinical tool in detecting cardiac stress levels in subjects to be tested for heart and lung disease, or the patients scheduled for a major surgery. CPDET is an involved test which requires the patient to breathe into a special mouthpiece and Electro cardiogram (ECG) of the subject is recorded before, during and after a stationary workout, e.g., on-the-spot cycling. Such tests can provide accurate and detailed heart and lung performance of the subject.

The inventors here have recognized several technical problems with such conventional tests, as explained below. Due to the use of specialised equipment, such test pose practical restrictions on their usage. People may fail to take such specialised tests at the onset of concerned disorders, which may worsen with time. Moreover, Current solutions pertaining to PPG based breathing monitoring are primarily able to compute breathing rate. However, there may be more markers to cardiac and lung problems hidden in the details of a breathing cycle. There exists sensors like Tidal Breathing Pattern Recorder (TBPR) however, these are invasive tests where the subject needs to blow into a pipe. Moreover, ubiquitous round the clock monitoring of breathing cycles is not available in state of art.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides method and system for extracting breathing patterns from PPG signals. The method includes designing, via one or more hardware processors, a filter for extracting breathing patterns from PPG signals. Herein designing the filter includes defining filter specifications for extraction of breathing pattern from the PPG signals, wherein the filter specifications comprising a type, an order and a cut-off frequency of the filter. Further designing the filter includes generating a transfer function associated with the filter specifications, and
 computing a plurality of filter coefficients using filtfilt function for allowing filtering of the PPG signals. The method further includes generating, using the filter comprising the plurality of filter coefficients, a filtered PPG signal by removing DC component from PPG signals obtained from a wearable device being worn by a subject via the one or more hardware processors. The filtered PPG signal indicative of the breathing pattern of the subject.

In another aspect, a system for extracting breathing patterns from PPG signals is provided. The system includes one or more memories; and one or more hardware processors, the one or more memories coupled to the one or more hardware processors, wherein the one or more hardware processors are capable of executing programmed instructions stored in the one or more memories to design a filter for extracting breathing patterns from PPG signals. To design the filter, the one or more hardware processors are configured by the instructions to define filter specifications for extraction of breathing pattern from the PPG signals, wherein the filter specifications comprising a type, an order and a cut-off frequency of the filter, generate a transfer function associated with the filter specifications, and compute a plurality of filter coefficients using filtfilt function for allowing filtering of the PPG signals. Further, the one or more hardware processors are further configured by the instructions to generate, using the filter comprising the plurality of filter coefficients, a filtered PPG signal by removing DC component from PPG signals obtained from a wearable device being worn by a subject. The filtered PPG signals are indicative of the breathing pattern of the subject.

In yet another aspect, a non-transitory computer-readable medium having embodied thereon a computer program for executing a method for extracting breathing patterns from PPG signals. The method includes designing, via one or more hardware processors, a filter for extracting breathing patterns from PPG signals. Herein designing the filter includes defining filter specifications for extraction of breathing pattern from the PPG signals, wherein the filter specifications comprising a type, an order and a cut-off frequency of the filter. Further designing the filter includes generating a transfer function associated with the filter specifications, and computing a plurality of filter coefficients using filtfilt function for allowing filtering of the PPG signals. The method further includes generating, using the filter comprising the plurality of filter coefficients, a filtered PPG signal by removing DC component from PPG signals obtained from a wearable device being worn by a subject via the one or more hardware processors. The filtered PPG signal indicative of the breathing pattern of the subject.

BRIEF DESCRIPTION OF THE FIGURES

The detailed description is described with reference to the accompanying figures. In the figures, the left-most digit(s) of a reference number identifies the figure in which the reference number first appears. The same numbers are used throughout the drawings to reference like features and modules.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

Cardiopulmonary disease prognosis can achieve therapeutic edge if the disorders can be detected and attended to at an early stage. Currently, Cardiopulmonary Exercise Test (CPET) acts as an important clinical tool in detecting cardiac stress levels in subjects to be tested for heart and lung diseases, or the patients scheduled for a major surgery. However, people may fail to take such specialised tests at the onset of concerned disorders, which may worsen with time.

According to American College of Cardiology Foundation/American Heart Association (ACCF/AHA), the most noteworthy and common symptoms of any cardiac disorder is shortness of breath (dyspnea) and fatigue coupled with palpitation if the body is subjected to an above-ordinary exertion. If the major physiological parameters can be recorded and studied during such spells while the subject is unobtrusively involved in routine activities, the need for specialised tests as discussed previously, can be eliminated and any anomalous behaviour in the stress-bearing capability of the body can be detected, hence providing the signs for any possible cardiopulmonary disorder at an earliest stage may be possible.

New York Heart Association (NYHA) classifies subjects into different classes denoting the stages in a possible cardiac disorder, where a Functional Capacity II, Objective Assessment B refers to the patients exhibiting dyspnoea, palpitation and fatigue in physical activities, which is the target detection class of the proposed platform. Said symptoms are almost ubiquitous among the cardiopulmonary disorders which are also reflected in the ACCF/AHA staging system where level C includes all the NYHA classes, and presents fatigue and dyspnoea as associated symptoms.

Estimation of physiological parameters like heart rate (HR) and blood pressure (BP) using PPG from mobile devices have been of prime interest to the researches. Using dedicated devices such as a pulse oximeter pose practical restrictions on automatic and on-the-go monitoring preventing their adoption in everyday life. Additionally, mobile phone camera has been extensively used in order to extract PPG signal and process it for heart rate estimation. There have been many researches targeting wearable device platform for extraction of PPG signals. In a conventional method, a reflective technique is used for extraction of PPG signals by using an ear-worn sensor to address application sensor variations. Another conventional method discloses the concept of wrist-worn wearables (or wearable devices) that have been researched extensively for HR and BP estimation.

In recent years, powerful devices such as smartwatches equipped with dedicated PPG sensors have been introduced. Said devices have quickly emerged as a choice of stylish wearables among the users, which have encouraged the research community to extend the PPG based research in this direction.

One conventional system uses FFT technique to infer breathing rate from the PPG cycles. Another conventional approach has tried to reproduce breathing cycles from PPG signals using MSPCA which is a wavelet-based adaptive multiscale principal component analysis, however such technique is not computationally very viable. Said conventional techniques and/or systems however aims at extracting respiration cycles from PPG with computational efficiency by enabling it to run on relatively constrained environments of smartwatches in real-time.

Various embodiments disclosed herein provides method and system for round-the-clock monitoring of a person's breathing pattern, and provides them with the breathing rate values in an unobtrusive manner, utilizing the PPG signal obtained from a wearable device such as a wrist wearable. The disclosed method is a computationally efficient solution that is devised to reconstruct breathing cycles from raw PPG signal recorded from the smartwatch, which enables the system to continuously monitor the subject's heart rate and breathing pattern online. The method achieves high accuracy when verified against a pre-calibrated flow-meter. As a sensing hardware, in an exemplary embodiment, the disclosed system utilizes a wearable device for instance a smartwatch, and at the same time boasts a powerful set of sensors, including Inertial Measurement Unit (IMU) and photoplethysmogram (PPG) sensor. Hence, the user is not subject to any special hardware. The system utilizes IMU in order to detect the spells of intensive activities, and uses PPG to extract the cardiac and breathing cycle information.

An important contribution of the disclosed method and system is to effectively design a filter for extraction of breathing patterns. A detailed description of the above described system is shown with respect to illustrations represented with reference to FIGS. 1A through 8.

The method(s) and system(s) for quality extraction of breathing patterns are further described in conjunction with the following figures. It should be noted that the description and figures merely illustrate the principles of the present subject matter. It will thus be appreciated that those skilled in the art will be able to devise various arrangements that, although not explicitly described or shown herein, embody the principles of the present subject matter and are included within its spirit and scope. Furthermore, all examples recited herein are principally intended expressly to be only for pedagogical purposes to aid the reader in understanding the principles of the present subject matter and the concepts contributed by the inventor(s) to furthering the art, and are to be construed as being without limitation to such specifically recited examples and conditions. Moreover, all statements herein reciting principles, aspects, and embodiments of the present subject matter, as well as specific examples thereof, are intended to encompass equivalents thereof.

Figure 1A:
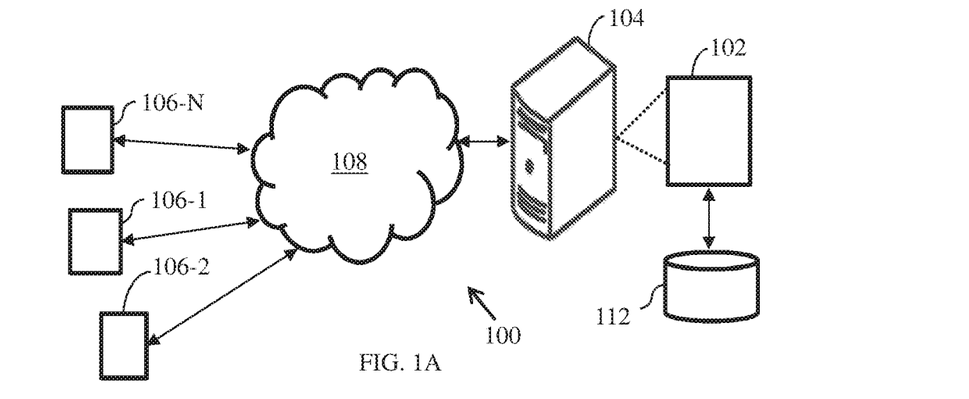
FIG. 1A illustrates a networking environment implementing system for extraction of breathing patterns from PPG signals, in accordance with an example embodiment.

FIG. 1A illustrates a network environment 100 implementing a system 102 for extraction of breathing patterns using PPG signals, according to an embodiment of the present subject matter. It will be noted herein that the PPG signals are considered herein for the extraction of breathing patterns since PPG signals can be very effective in determining cardiac cycle due to their non-invasiveness and accurate results. PPG signals also contain information about the systolic/diastolic pressure difference in alternating current (AC) component thereof. It is also possible to extract the respiratory cycle from PPG. The PPG sensor embodied in a wearable device such as a smartwatch facilitates in physiological monitoring in a non-obtrusive manner, since it does not require action from user's perspective. Thus, the disclosed embodiments are capable of extracting breathing patterns from the PPG signals derived from user's wearable devices such as smartwatch (when worn by the user), as will be explained further in detail below.

Figure 1B:
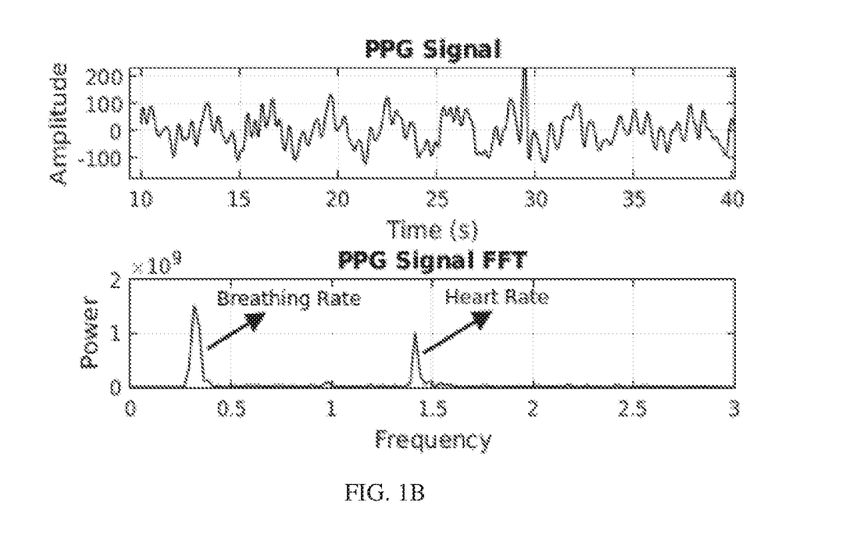
FIG. 1B illustrates a PPG Signal and its Corresponding Dual-Peaked Frequency Equivalent, in accordance with an example embodiment.

In an embodiment, the system 102 may receive inputs from the user's wearable device in form of PPG signals. There is a high coherence between the respiratory cycles and PPG signals. A typical PPG signal and its corresponding frequency spectrum is shown in FIG. 1B, where the peaks pertaining to heart rate and breathing rate can be seen. In order to enable a detailed analysis at a later stage, full breathing cycles can prove to be more useful than only the respiratory rate. In an embodiment, the system 102 for monitoring may be embodied on the wearable device such as the smartwatch, without any special add-on hardware requirement, thereby providing a computationally efficient way of extracting breathing patterns from the PPG signals.

Figure 3:
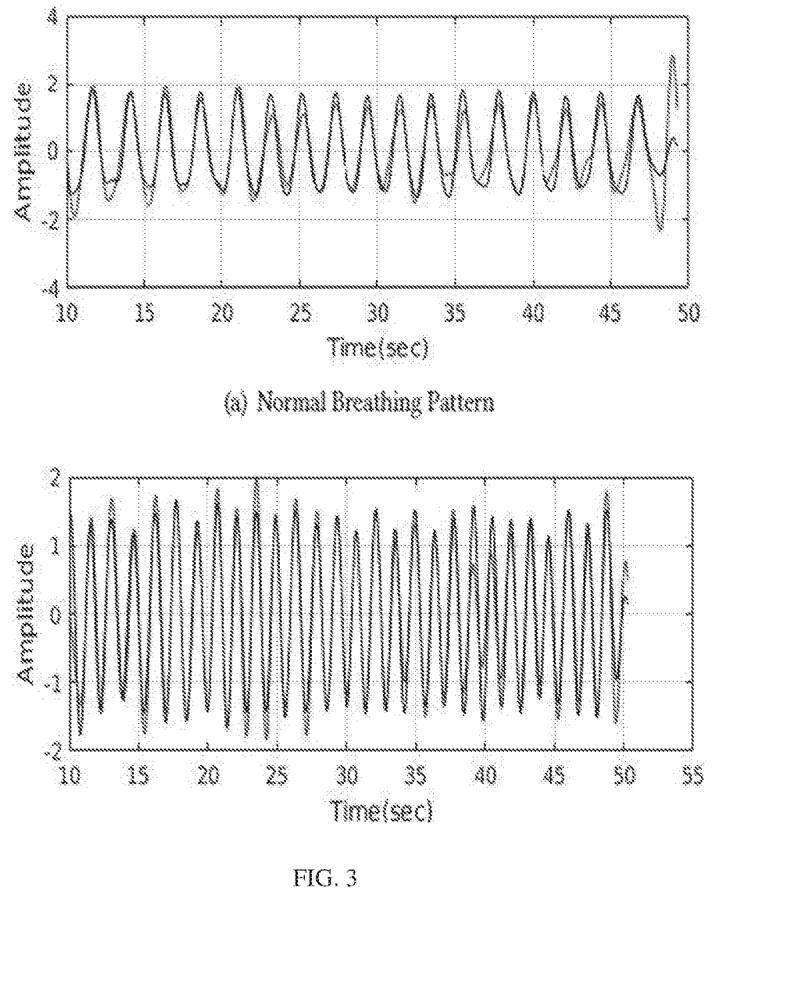
FIG. 3 illustrate a Coherence in breathing patterns between that extracted from PPG and TBPS, in accordance with an example embodiment.

In an embodiment, raw PPG data is collected from the PPG sensor embodied in the wearable device (such as the smartwatch) and is resampled to a rate of 50 Hz to obtain a resampled PPG data. The resampled PPG data is analysed by the system on a windowed basis. A zero phase forward-reverse filtering is performed on the resampled PPG data using a Butterworth HR filter. Typically, a person's normal breathing rate falls between 15-25 breaths/min. During fatigued spells, the shortness of breath can cause the breathing rate to rise to 50-60 breaths/min. Hence, said filter's pass-band is specified as 0.25 Hz -1 Hz. FIG. 3 shows a comparison between an extracted breathing pattern from the PPG and the same from a TBPS. It is evident that the patterns match appreciably, proving the effectiveness of the disclosed method.

Figure 2:
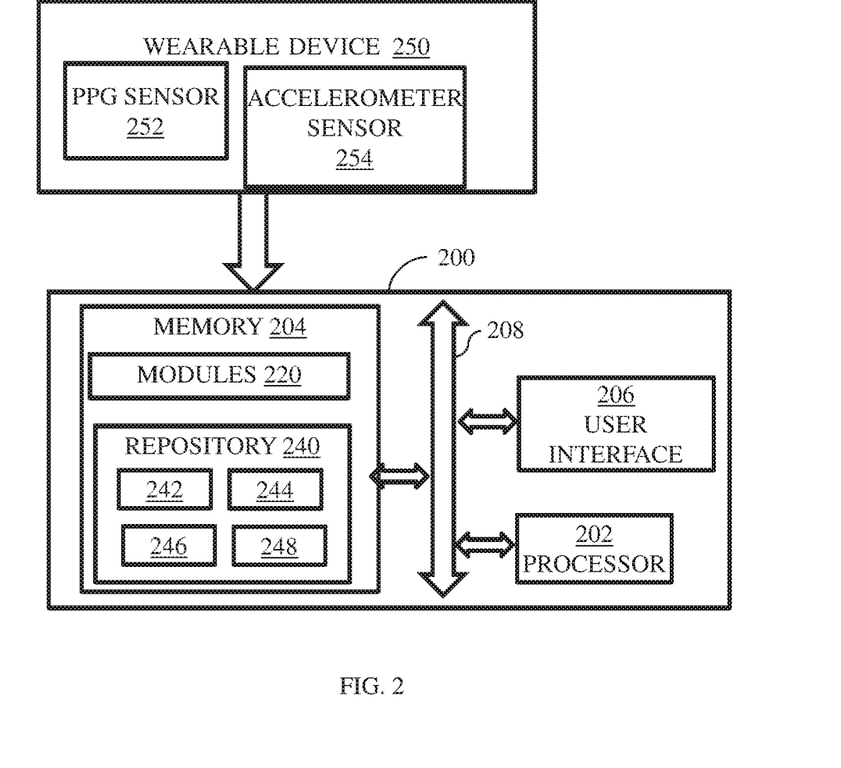
FIG. 2 illustrates a block diagram of a system for extraction of breathing patterns from PPG signals, in accordance with an example embodiment.

As described above, the system may be embodied in a wearable device worn by the user. In an alternative embodiment, the system 102 may be embodied in a computing device, for instance a computing device 104 communicably coupled with the wearable device. In an embodiment, the computing device may be an example of a server. Herein, although the present disclosure is explained considering that the system 102 is implemented on a server, it may be understood that the system 102 may also be implemented in a variety of computing systems, such as a laptop computer, a desktop computer, a notebook, a workstation, a cloud-based computing environment and the like. In one implementation, the system 102 may be implemented in a cloud-based environment. It will be understood that the system 102 may be accessed by multiple users through one or more user devices 106-1, 106-2 . . . 106-N, collectively referred to as user devices 106 hereinafter, or applications residing on the user devices 106. Examples of the user devices 106 may include, but are not limited to, a portable computer, a personal digital assistant, a handheld device, a Smartphone, a Tablet Computer, a workstation and the like. The user devices 106 are communicatively coupled to the system 102 through a network 108. Herein, the users of the user-devices 106 may include users wearing similar wearable devices.

In an embodiment, the network 108 may be a wireless or a wired network, or a combination thereof. In an example, the network 108 can be implemented as a computer network, as one of the different types of networks, such as virtual private network (VPN), intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP). and Wireless Application Protocol (WAP), to communicate with each other. Further, the network 108 may include a variety of network devices, including routers, bridges, servers, computing devices, storage devices. The network devices within the network 108 may interact with the system 102 through communication links.

As discussed above, the system 102 may be implemented in a computing device 104, such as a hand-held device, a laptop or other portable computer, a tablet computer, a mobile phone, a FDA, a smartphone, and a wearable device such as a smart watch. The system 102 may also be implemented in a workstation, a mainframe computer, a server, and a network server. In an embodiment, the system 102 may be coupled to a data repository, for example, a repository 112. The repository 112 may store data processed, received, and generated by the system 102. In an alternate embodiment, the system 102 may include the data repository 112. The components and functionalities of the system 102 are described further in detail with reference to FIG. 2.

FIG. 2 illustrates a block diagram of a system 200 for breathing pattern extraction from PPG signals, in accordance with an example embodiment. The system 200 may be an example of the system 102 (FIG. 1A). In an example embodiment, the system 200 may be embodied in, or is in direct communication with the system, for example the system 102 (FIG. 1). It will be understood that the system 200 for breathing pattern extraction can be used in various applications, including but not limited to, intensive activity detection, fatigue detection, and so on.

The system 200 includes or is otherwise in communication with one or more hardware processors such as a processor 202, at least one memory such as a memory 204, and an I/O interface 206. The processor 202, memory 204, and the I/O interface 206 may be coupled by a system bus such as a system bus 208 or a similar mechanism. The I/O interface 206 may include a variety of software and hardware interfaces, for example, a web interface, a graphical user interface, and the like The interfaces 206 may include a variety of software and hardware interfaces, for example, interfaces for peripheral device(s), such as a keyboard, a mouse, an external memory, a camera device, and a printer.

Further, the interfaces 206 may enable the system 102 to communicate with other devices, such as web servers and external databases. The interfaces 206 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 206 may include one or more ports for connecting a number of computing systems with one another or to another server computer. The I/O interface 206 may include one or more ports for connecting a number of devices to one another or to another server.

The hardware processor 202 may be implemented as one or more microprocessors, microcomputers, microcontrollers, digital signal processors, central processing units, state machines, logic circuitries, and/or any devices that manipulate signals based on operational instructions. Among other capabilities, the hardware processor 202 is configured to fetch and execute computer-readable instructions stored in the memory 204.

The memory 204 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 204 includes a plurality of modules 220 and a repository 240 for storing data processed, received, and generated by one or more of the modules 220. The modules 220 may include routines, programs, objects, components, data structures, and so on, which perform particular tasks or implement particular abstract data types.

The repository 240, amongst other things, includes a system database 242 and other data 244. The other data 244 may include data generated as a result of the execution of one or more modules in the modules 220. The repository 240 is further configured to maintain PPG data 246 and motion data 248. The PPG data 246 may be obtained from PPG sensor(s) 252 embodied in the wearable device, such as wearable device 250 and may contain data associated with raw PPG signal. The motion data 248 may contain data associated with intense activity being performed by the user. The motion data 248 may be captured from sensors such as accelerometer 254 and barometer embodied in the wearable device 250. The motion data provide information associated with the intense activity being performed by the user. Herein, it will be understood that if the major physiological parameters associated with a user can be recorded and studied while the subject is unobtrusively involved in activities, the need for specialised tests to detect abnormal stress causing condition, can be eliminated and any anomalous behavior in the stress-bearing capability of the body can be detected, hence provides the signs for any possible cardio-pulmonary disorder at an earliest stage possible. For example, such monitoring of parameters can disclose/detect the patients exhibiting dyspnea, palpitation and fatigue in physical activities, and so on.

In an embodiment, the system 200 takes raw PPG signals (or PPG data) and motion data obtained from user's wearable device as input for pre-processing. The PPG signal taken from the wrist wearable may contain noise and may be distorted, and accordingly may be difficult to work with. Hence, the interpolated and windowed signal is then pre-processed, i.e., DC component of the signal is removed, and the signal is filtered by a filter.

Pre-processing the raw PPG signals provides PPG signals associated with a window size and a sampling frequency suitable for the breathing pattern extraction. In an embodiment, the pre-processing the raw PPG signal and the motion data includes interpolating signals received from the PPG sensor and motion sensors to bring them to a uniform sampling frequency, $F_s$ of 50 Hz. The interpolated PPG signals are then taken window-wise, for further analysis, as explained further below in the description. Herein, the window size or windows of interest refers to the windows in which it is preferred to analyse PPG data so as to compute physiology of the subject. In general, such windows of interest correspond to the subject being in rest position before and after performing some activity. As explained above, to detect a subject is engaged in an activity, the system 200 receives inputs from the motion sensors such as accelerometer and/or barometer. Accelerometer is a sensor that can detect any acceleration force exerted on the (3-axes: x, y, z of the) device. To detect the state of the device (i.e. whether the device worn by the user is in rest or in motion), the system 200 calculates the resultant value of the accelerometer readings. In the rest position of the user, the resultant value is nearly equal to g (i.e. 9.8 m/s$^2$) whereas during motion the resultant value fluctuates between 0 to +4 g. Since the wearable device is worn by the subject, by the help of accelerometer sensor, the system can distinctively detect motion and rest phases of the subject. In an embodiment, the system 200 computes mean and standard deviation of the accelerometer signal to determine whether the subject is in motion or at rest. If the subject is determined to be in motion, the PPG signal captured corresponding to said window is discarded. If, however, the system determines the subject to be at rest or in rest position, the PPG signal captured corresponding to said window is considered for further processing for breathing pattern extraction. In an embodiment, said further processing includes generating a plurality of filter coefficients, as will be described later in the description.

In an example embodiment, the window size may be around 10 seconds. In an embodiment, since the wearable device is continuously worn by the user, the system 200 is able to continuously monitor the inputs such as the PPG signal of the user, for example, during rest and during motion. Elongated periods of rest (such as 10 minutes or more), are one type of windows of interest, whereby the system can detect physiological parameters of the user when the user is normal and relaxed. The other types of windows of interest may be just after the user has performed some activity for some time. The reason for selection of said period as window of interest is because, there are visible changes in the physiological parameters (increased Heart rate and breathing rate) of the user just after performing some strenuous activity (like climbing stairs, running, and so on). The changes observed in the physiological parameters with respect to rest and just after motion windows of interest can be possibly used to study for non-specific bio-markers.

Herein, the choice of the window size is an important factor, as it determines the accuracy of the system but in the present case, there is a trade-off between accuracy, latency and number of potent measurements. For example, if window size is say 30 sec, the accuracy is +−1 BrPM, but due to large window size the system has high latency i.e. the system needs to wait for long (30 secs) to obtain one output. Hence, it is important to decide not to sacrifice on accuracy to get quick results or get high accuracy for late results. Since all the accuracy of +−3 BrPM is acceptable, the system can be designed 10 seconds window size. Here, 10 seconds window size is considered to attain an accuracy of +−3 BrPM, and get the BR values at a fairly acceptable interval, thereby solving the accuracy versus latency trade-off for a healthcare application As previously described, upon determination of the subject to be at rest, the system generates the plurality of filter coefficients for filtering the processed PPG signal. In an embodiment, the system generates said filter coefficients by removing DC component from the PPG signals. Herein, the filtered PPG signal indicative of the breathing pattern of the subject.

In an embodiment, the system 200 is capable of designing a filter for extracting breathing patterns from PPG signals. Herein, the filter is designed such that it can effectively separate out breathing signal from a pulse-measurement sensor signal like PPG. In an embodiment, designing the filter includes defining filter specifications for extraction of breathing pattern from the PPG signals. In an embodiment, the filter specifications include a type, an order and a cut-off frequency of the filter. In an example embodiment, the filter specifications for breathing pattern extraction may include IIR Butter-worth band-pass filter of order 4, with a cut-off frequency of 0.2-1 Hz, as will be explained further in detail below.

Designing a filter consists of developing specifications appropriate to the problem (for example, a second-order low pass filter with a specific cut-off frequency), and then producing a transfer function which meets the specifications:

$$H(z)=B(z)/A(z)=(b0+b1*z^{-1}+b2*z^{-2}+\ldots+bN*z^{-N})/(1+a1*z^{-1}+a2*z^{-2}+\ldots+aN*z^{-N}) \quad (1)$$

where, a is a matrix 3×3 [a0, a1, . . . a8], and
b is a matrix 3×3 [b1, b1, . . . b8].
Here, a and b are coefficients of the transfer function fed as input to the filter.

This is the form for a recursive filter, which typically leads to an infinite impulse response (IIR) behaviour, but if the denominator is made equal to unity i.e. no feedback, then this becomes an FIR or finite impulse response filter. In order to achieve good results in extraction of breathing pattern and calculation of breathing rate from a wearable-PPG signal, the filter should be able to efficiently eliminate noise, while keeping the computation as simple as possible. This is very important, especially in case of breathing pattern extraction from wrist PPG signal, as the signal inherently contains a lot of noise owing to the wrist movements and change of position of sensor while the subject is wearing the wrist wearable.

The important parameters that determine the quality of filter to get the desired results are the type of filter and the order of filter. The order of a filter usually refers to the number of components (capacitors and inductors, not resistors or transistors) or the number of computations required for the filter, that affect the 'steepness' or 'shape' of the filter's frequency response. A first-order recursive filter will only have a single frequency-dependent component. This means that the slope of the frequency response is limited to 6 dB per octave. For many purposes, this is not sufficient. To achieve steeper slopes, higher-order filters are required. Hence, the disclosed embodiments have implemented the IIR Butterworth Filter of order 4, which helps in achieving a better shape of frequency response, while keeping in mind the stability of the filter and reducing computational complexities at the same time.

For breathing pattern extraction, the filter design includes an IIR Butterworth band-pass filter of order 4, with a cut-off frequency of 0.2-1 Hz, so as to include slow (12-15 BrPM) as well as fast (50-55 BrPM) breathing rates. The primary advantage of IIR filters over FIR filters is that they typically meet a given set of specifications with a much lower filter order than a corresponding FIR filter and thus, IIR filter is selected for breathing pattern extraction. The Butterworth filter is a type of signal processing filter designed to have as flat frequency response as possible in the passband. The frequency response of the Butterworth filter is maximally flat (i.e. has no ripples) in the passband and rolls off towards zero in the stopband, unlike other filter types that have non-monotonic ripple in the passband and/or the stopband.

Thus, the filter is to be designed in such a way that the noise is efficiently eliminated and the breathing cycle information is obtained accurately. The coefficients are calculated for these parameters, and the filtering is done in forward as well as reverse direction (Zero-phase forward and reverse digital IIR filtering), thereby preserving the frequency information and providing zero phase distortion. The filter design is perfected over a number of signals gathered from multiple subjects in relaxed and laboured breathing scenarios. The cut-off frequencies are decided empirically because typical breathing rates are much lower like 15-30 times a minute at max as per state-of-the-art. Using the above mentioned frequencies, the selected filter order, and the data sampling rate, the system 200 computes the filter coefficients a & b (in equation 1) using filtfilt function which allows for a non-causal, zero-phase filtering approach which eliminates the nonlinear phase distortion of an IIR filter. As is understood, the filtfilt function performs zero-phase digital filtering by processing an input data in both the forward and reverse directions. After filtering the data in the forward direction, filtfilt reverses the filtered sequence and runs it back through the filter. The results of filtfilt has characteristics, including, zero phase distortion, a filter transfer function equal to the squared magnitude of the original filter transfer function, and a filter order that is double the order of the filter specified by b and a.

The system 200 normalizes the filtered time signal with respect to its mean and standard deviation (Standard score=data−mean/stdev) to eliminate amplitude discrepancies which may lead to differences with the actual breathing patterns. There are various means of normalizing a time-series data, and the above technique is one of them. The disclosed normalization technique for breathing signal is based on an assumption that breathing is a slow changing bio-marker hence having a zero mean and unit stddev gives relative amplitude in a better form. Thus, with the help of the normalized signal, the pre-processed PPG time-signal can be determined to have high correlation with the actual breathing pattern signal received from a TBPR device, with the help of their Pearson Coefficient. The pre-processed PPG signal contains significant information about the breathing pattern of the subject, and can be further used for reconstructing breathing cycles and studying whether the subject has cardiopulmonary related issues.

The system 200 analyses the PPG signal, after pre-processing, in frequency domain, by computing its Fourier Transform (FFT) and obtaining power spectrum. The number of FFT points is typically chosen as 512, for a 10 second window and 50 Hz signal. This can be configured to 2048 points (40 second window) for getting a better accuracy for windows of interest. From the power spectrum, the highest isolated peak is taken as breathing frequency and is used to calculate breathing rate in Breaths per minute (BrPM). The breathing rate in (BrPM) is the number of breaths (inhale and exhale cycle) that happen over a time span of 1 minutes.

Herein the FFT point (i.e. the highest isolated peak) is selected which allows user to increase resolution for windows of interest. Thus, the outcome of the disclosed analysis provides both the average amplitude and frequency of breathing for a 10 second window of an individual. This can be possibly used for study of non-specific bio-markers for a number of conditions like sleep apnea, hypertension, asthma, and so on. An example flow-diagram of a method for breathing pattern extraction from PPG signal is described further with reference to FIG. 4.

Figure 4:
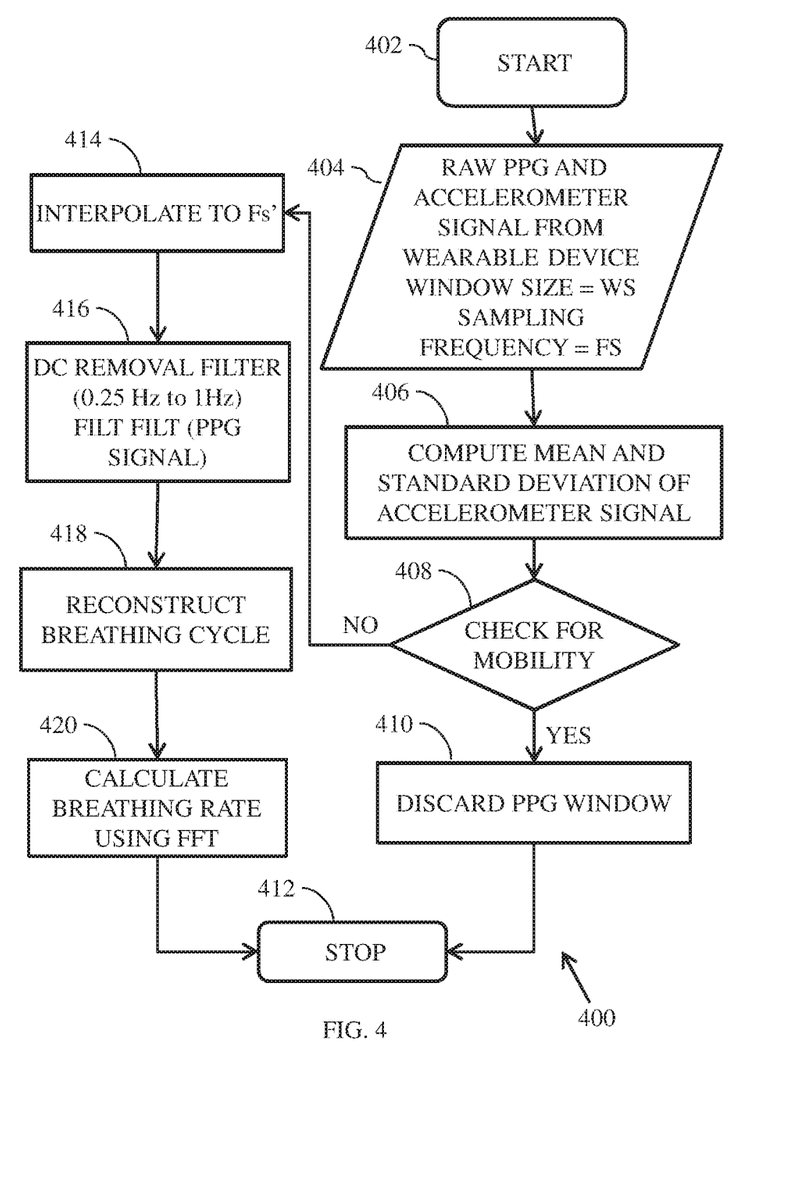
FIG. 4 illustrates an example flow diagram for a method for extraction of breathing patterns from PPG signals, in accordance with an example embodiment.

FIG. 4 illustrates an example flow diagram of a method 400 for breathing pattern extraction from PPG signal, in accordance with an example embodiment. Breathing pattern refers to the amplitude of air flow during a inhale-exhale cycle, as illustrated in FIG. 3.

At 402, the method 400 is initiated and raw PPG signal and accelerometer signals are acquired from a wearable device, for example a smart watch, at 404. Herein, it will be understood that for the brevity of discussion, various embodiments of the disclosure are presented by considering the wearable device as a smartwatch. However, in various embodiments, the wearable device may include other such devices that can be worn by the subject and are capable of embodying a PPG sensor and an accelerometer. The window size and sampling frequency of the PPG signal are considered as described with reference to FIG. 2.

At 406, mean and standard deviation of the accelerometer signal are computed. Based on the mean and standard deviation of the accelerometer signal, it is determined at 408, whether the subject is mobile or not. If it is determined that the subject is mobile, the PPG signal for said window is discarded at 410, and the method terminates at 412.

If however, at 408 it is determined that the subject is not mobile, the PPG signal is considered for further analysis. For example, at 414, the PPG signal is interpolated, and its DC component is filtered at 416 using IIR Butterworth band-pass filter of order 4, with a cut-off frequency of 0.2-1 Hz. The breathing cycle is reconstructed at 418 to obtain the breathing pattern, and breathing rate is computed using the FFT at 420. An example scenario for describing experimental results corresponding to the disclosed method and system is explained below.

Figure 5:
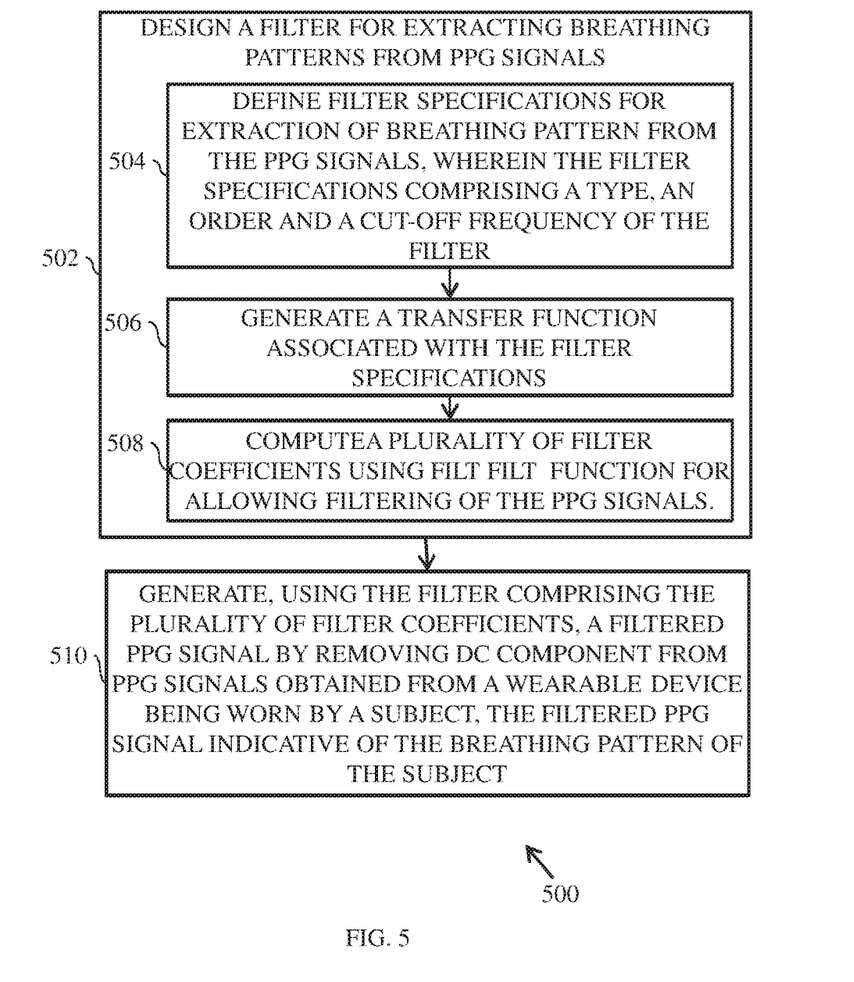
FIG. 5 illustrates an example flow diagram for a method for extraction of breathing patterns from PPG signals, in accordance with an example embodiment.

FIG. 5 illustrates an example method 500 for breathing pattern extraction from PPG signal, in accordance with an example embodiment. The method 500 may be described in the general context of computer executable instructions. Generally, computer executable instructions can include routines, programs, objects, components, data structures, procedures, modules, functions, etc., that perform particular functions or implement particular abstract data types. The method 500 may also be practiced in a distributed computing environment where functions are performed by remote processing devices that are linked through a communication network. The order in which the method 500 is described is not intended to be construed as a limitation, and any number of the described method blocks can be combined in any order to implement the method 500, or an alternative method. Furthermore, the method 500 can be implemented in any suitable hardware, software, firmware, or combination thereof. In an embodiment, the method 500 depicted in the flow chart may be executed by a system, for example, the system 200 of FIG. 2. In an example embodiment, the system 200 may be embodied in an exemplary computer system.

Referring to FIG. 5, the method for breathing pattern extraction from PPG signals is initiated at 502, where a filter is designed for extracting breathing patterns from PPG signals. The designing of the filter includes defining filter specifications for extraction of breathing pattern from the PPG signals at 502. Herein, the filter specifications includes a type, an order and a cut-off frequency of the filter. Further designing of the filter includes generating a transfer function associated with the filter specifications, at 506 and computing a plurality of filter coefficients using filtfilt function for allowing filtering of the PPG signals, at 508. In an embodiment the filter is designed by using the system, for example the system 200 (as is described with reference to FIG. 2). At 510, the method 500 includes generating filtered PPG signals using the filter comprising the plurality of filter coefficients, by removing DC component from PPG signals obtained from a wearable device being worn by a subject. The filtered PPG signal are indicative of the breathing pattern of the subject.

Figure 6:
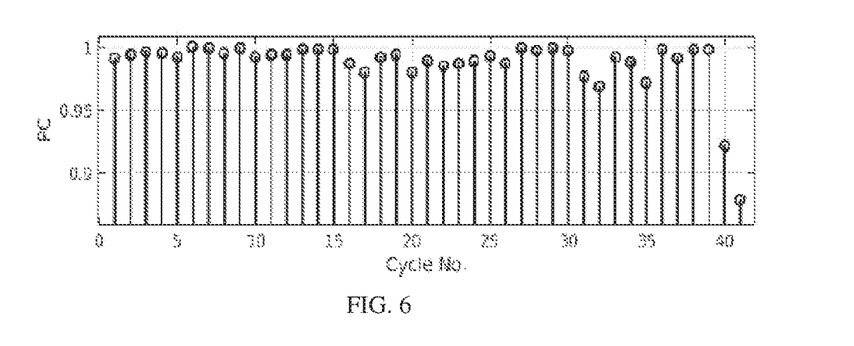
FIG. 6 illustrates PC calculated for each breathing cycle for a single best session, in accordance with an example embodiment.
Figure 7:
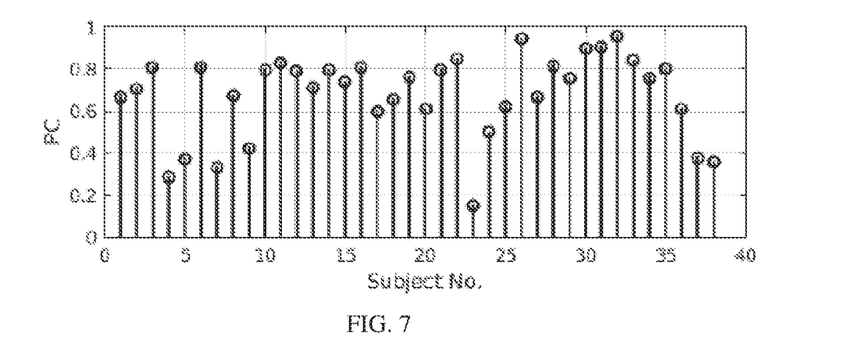
FIG. 7 illustrates PC calculated for each full session, in accordance with an example embodiment.
Figure 8:
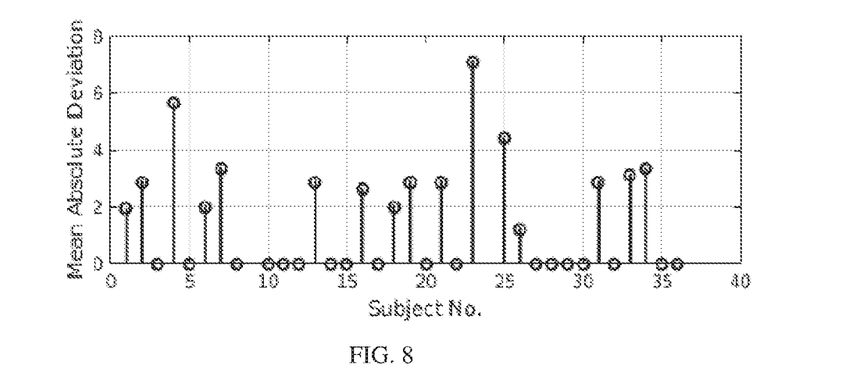
FIG. 8 illustrates mean absolute deviation in breathing rate for all sessions, in accordance with an example embodiment.

An example scenario for breathing pattern extraction from PPG signal is described further in the description by referring to FIGS. 6-8.

Example Scenario

In order to validate the accuracy of breathing pattern extraction method and system, the experimental results are provided. 38 sessions of data are collected from 19 subjects with age group of 31±8 years. Two data streams were collected in each session, one from a TBPS as ground truth, and another from a Samsung Gear S2™ smartwatch which was worn by the subjects on their wrist during the sessions. The subjects were asked to breathe at different rates during the session to ensure a wide spectrum of breathing frequencies is covered. Each session was approximately 60 s of duration. It was analysed and processed the data from 10 s-50 s. It was observed that the method is able to extract the breathing cycles from PPG very accurately, and shows a very high correlation to those obtained from the TBP device. A Pearson's Correlation (PC) is estimated for each session between these two streams of data. PC is a bivariate tool which expresses the strength of correlation between two random variable X and Y and is calculated as:

$$\rho(X, Y) = \frac{\text{Cov}(X, Y)}{\sigma_X \sigma_Y}$$

where Cov is covariance, and $\sigma$ is the standard deviation.

Following figures, FIGS. 6, 7 and 8 illustrates results are derived from the experiment:

FIG. 6 shows PC calculated for each breathing cycle for a single best session, where the average PC stands at 0.987 proving the high accuracy of the disclosed breathing cycle extraction method. It is also observed that the occurrence of respiratory peaks in the PPG-extracted signal was accurate within an average of 0.5 s, cementing the physiological effect of respiration on the PPG. FIG. 7 shows PC calculated for each full session, where 30 out of 38 sessions have an encouraging PC>0.5. The breathing rates estimated from TBPS and PPG are compared by calculating Mean Absolute Deviation (MAD) for each session (FIG. 8; 3 outliers removed). Average MAD for all the sessions was determined to be only 1.5.

Various embodiments disclosed herein provide method and system for breathing pattern extraction from PPG signals. The disclosed system can be installed in an electronic device such as a wearable (for example a smart watch), and hence the proposed system is easily portable and can be utilized for continuous monitoring. Moreover such wearable devices includes powerful set of sensors, including IMU and PPG. Hence the user is not subject to any special hardware. The system uses IMU in order to detect the spells of intensive activities, and uses PPG to extract the cardiac and breathing cycle information. The system uses PPG from wrist which is an indirect marker of Breathing rate. In addition, the system utilizes a forward-reverse zero phase IIR Butterworth band-pass filter designed specifically to get the noise-removed PPG signal in Respiration range.

In an embodiment, the system involves itself with providing an opportunistic sensing of the physiological parameters pertaining to detection of palpitation and dyspnea, and detecting the fatigued states around the physically intensive spells that the user undertakes as routine tasks. In addition to a ubiquitous monitoring, the platform can be used as a longitudinal clinical assessment tool, where a specialist can direct the subject to perform certain activities with customisable parameters like pre-workout resting duration etc. Physiological parameters are recorded before and after the activity. Additionally information like subject's current fitness level (normal, moderately sick or acutely sick), comfort level while doing activity etc. can also be collected in the form of a questionnaire to assist the specialist with a more in-depth analytics of the recorded parameters.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

What is claimed is:

1. A processor-implemented method for extracting breathing patterns from photoplethysmogram (PPG) signals, the method comprising:
   obtaining, from an accelerometer sensor embodied in a wearable device, an accelerometer signal indicative of motion of a subject;
   pre-processing, via one or more hardware processors, raw PPG signals to obtain the PPG signals associated with a window size and a sampling frequency suitable for the breathing pattern extraction, wherein the step of pre-processing the raw PPG signals includes interpolating signals received from the accelerometer sensor and to bring the PPG signals to a uniform sampling frequency;
   computing, via the one or more hardware processors, mean and standard deviation values of the accelerometer signal to determine whether the subject is in motion; and
   performing, via the one or more hardware processors, based on the determination, one of:
   discarding the PPG signals captured from the wearable device upon determination of the subject to be in motion, and
   generating a plurality of filter coefficients upon determination of the subject to be in rest position;
   designing, via the one or more hardware processors, a filter for extracting the breathing patterns from the PPG signals, wherein designing the filter comprises:
   defining filter specifications for extraction of a breathing pattern from the PPG signals, wherein the filter specifications comprises a type, an order, and a cut-off frequency of the filter, and wherein the filter specifications for the extraction of the breathing pattern further comprises Infinite Impulse response (IIR) Butter-worth band-pass filter of order 4, with the cut-off frequency of 0.2-1 Hz to include a slow breathing rate of 12-15 Breaths per Minute (BrPM) up to fast breathing rate of 50-55 BrPM,
   generating a transfer function associated with the filter specifications, and
   computing the plurality of filter coefficients using filtfilt function for allowing filtering of the PPG signals, wherein the filtfilt function performs zero-phase digital filtering by processing an input data in both the forward and reverse directions;
   generating, using the filter comprising the plurality of filter coefficients, filtered PPG signals by removing DC component from the PPG signals obtained from the wearable device configured to be worn by the subject via the one or more hardware processors, the filtered PPG signals indicative of the breathing pattern of the subject;
   normalizing, via the one or more hardware processors, the filtered PPG signals with respect to the mean and standard deviation values;
   analyzing, via the one or more hardware processors, the filtered PPG signal in frequency domain, by computing Fourier Transform (FFT) and obtaining power spectrum, wherein from the power spectrum, a highest isolated peak is taken as breathing frequency and is used to calculate the breathing rate in BrPM;
   detecting, via the one or more hardware processors, anomalous behavior in stress-bearing capability of body of the subject based on the calculated breathing rate, identifying signs of cardiopulmonary disorders at an earliest stage, in the subject based on the detection of anomalous behavior, wherein the cardiopulmonary disorders include fatigue during physically intensive spells, palpitation and dyspnea; and
   providing, via the one or more hardware processors, an opportunistic sensing of one or more physiological parameters based on the detected anomalous behavior, wherein the one or more physiological parameters are recorded before and after an activity.

2. The method as claimed in claim 1, wherein the window size is around 10 seconds.

3. A system for extracting breathing patterns from photoplethysmogram (PPG) signals, the system comprising:
   one or more memories; and
   one or more hardware processors, the one or more memories coupled to the one or more hardware processors, wherein the one or more hardware processors are capable of executing programmed instructions stored in the one or more memories to:
   obtain, from an accelerometer sensor embodied in a wearable device, an accelerometer signal indicative of motion of a subject;

pre-process, raw PPG signals to obtain the PPG signals associated with a window size and a sampling frequency suitable for the breathing pattern extraction, wherein pre-processing the raw PPG signals includes interpolating signals received from the accelerometer sensor and to bring the PPG signals to a uniform sampling frequency;

compute, mean and standard deviation values of the accelerometer signal to determine whether the subject is in motion; and perform, based on the determination, one of:
discard the PPG signals captured from the wearable device upon determination of the subject to be in motion, and
generate the plurality of filter coefficients upon determination of the subject to be in rest position;

design a filter for extracting the breathing patterns from the PPG signals, wherein designing the filter comprises:
defining filter specifications for extraction of a breathing pattern from the PPG signals, wherein the filter specifications comprising a type, an order and a cut-off frequency of the filter, and wherein the filter specifications for the extraction of the breathing pattern further comprises Infinite Impulse response (IIR) Butter-worth band-pass filter of order 4, with the cut-off frequency of 0.2-1 Hz to include a slow breathing rate of 12-15 Breaths per Minute (BrPM) up to fast breathing rate of 50-55 BrPM,
generating a transfer function associated with the filter specifications, and
computing the plurality of filter coefficients using filtfilt function for allowing filtering of the PPG signals, wherein the filtfilt function performs zero-phase digital filtering by processing an input data in both the forward and reverse directions;

generate, using the filter comprising the plurality of filter coefficients, filtered PPG signals by removing DC component from the PPG signals obtained from the wearable device configured to be worn by the subject, the filtered PPG signals indicative of the breathing pattern of the subject;

normalize, the filtered PPG signals with respect to the mean and standard deviation values;

analyze the filtered PPG signal in frequency domain, by computing Fourier Transform (FFT) and obtaining power spectrum, wherein from the power spectrum, a highest isolated peak is taken as breathing frequency and is used to calculate the breathing rate in BrPM; and detect anomalous behavior in stress-bearing capability of body of the subject based on the calculated breathing rate, to identify signs of cardiopulmonary disorders at an earliest stage, in the subject based on the detection of anomalous behavior, wherein the cardiopulmonary disorders include fatigue during physically intensive spells, palpitation and dyspnea; and provide an opportunistic sensing of one or more physiological parameters based on the detected anomalous behavior, wherein the one or more physiological parameters are recorded before and after an activity.

4. The system as claimed in claim 3, wherein the window size is around 10 seconds.

5. One or more non-transitory machine readable information storage mediums comprising one or more instructions which when executed by one or more hardware processors causes the one or more hardware processor to perform a method for extracting breathing patterns from photoplethysmogram (PPG) signals, said method comprising:

obtaining, from an accelerometer sensor embodied in a wearable device, an accelerometer signal indicative of motion of a subject;

pre-processing raw PPG signals to obtain the PPG signals associated with a window size and a sampling frequency suitable for the breathing pattern extraction, wherein the step of pre-processing the raw PPG signals includes interpolating signals received from the accelerometer sensor and to bring the PPG signals to a uniform sampling frequency;

computing, mean and standard deviation values of the accelerometer signal to determine whether the subject is in motion; and performing, based on the determination, one of:
discarding the PPG signals captured from the wearable device upon determination of the subject to be in motion, and
generating the plurality of filter coefficients upon determination of the subject to be in rest position;

designing, via the one or more hardware processors, a filter for extracting the breathing patterns from the PPG signals, wherein designing the filter comprises:
defining filter specifications for extraction of a breathing pattern from the PPG signals, wherein the filter specifications comprises a type, an order, and a cut-off frequency of the filter, and wherein the filter specifications for the extraction of the breathing pattern further comprises Infinite Impulse response (IIR) Butter-worth band-pass filter of order 4, with the cut-off frequency of 0.2-1 Hz to include a slow breathing rate of 12-15 Breaths per Minute (BrPM) up to fast breathing rate of 50-55 BrPM,
generating a transfer function associated with the filter specifications, and
computing the plurality of filter coefficients using filtfilt function for allowing filtering of the PPG signals, wherein the filtfilt function performs zero-phase digital filtering by processing an input data in both the forward and reverse directions;

generating, using the filter comprising the plurality of filter coefficients, filtered PPG signals by removing DC component from the PPG signals obtained from the wearable device configured to be worn by the subject via the one or more hardware processors, the filtered PPG signals indicative of the breathing pattern of the subject;

normalizing the filtered PPG signals with respect to the mean and standard deviation values;

analyzing, the filtered PPG signal in frequency domain, by computing Fourier Transform (FFT) and obtaining power spectrum, wherein from the power spectrum, a highest isolated peak is taken as breathing frequency and is used to calculate the breathing rate in BrPM; and detecting, anomalous behavior in stress-bearing capability of body of the subject based on the calculated breathing rate, identify signs of cardiopulmonary disorders at an earliest stage, in the subject based on the detection of anomalous behavior, wherein the cardiopulmonary disorders include fatigue during physically intensive spells, palpitation and dyspnea; and providing an opportunistic sensing of one or more physiolo ig cal parameters based on the detected anomalous behavior, wherein the one or more physiological parameters are recorded before and after an activity.

6. The one or more non-transitory machine readable information storage mediums of claim 5, wherein the window size is around 10 seconds.

\* \* \* \* \*